(12) United States Patent
Levinson

(10) Patent No.: US 11,139,088 B2
(45) Date of Patent: Oct. 5, 2021

(54) GRID FOR X-RAY IMAGING

(71) Applicant: alephFS—Systems for Imaging, Haifa (IL)

(72) Inventor: Reuven Levinson, Haifa (IL)

(73) Assignee: ALEPHFS—SYSTEMS FOR IMAGING, Haifa (IL)

(*) Notice: Subject to any disclaimer, the term of this patent is extended or adjusted under 35 U.S.C. 154(b) by 0 days.

(21) Appl. No.: 16/438,805

(22) Filed: Jun. 12, 2019

(65) Prior Publication Data

US 2020/0395141 A1    Dec. 17, 2020

(51) Int. Cl.
| G21K 1/00 | (2006.01) |
| G21K 1/02 | (2006.01) |
| A61B 6/00 | (2006.01) |
| G21K 1/10 | (2006.01) |

(52) U.S. Cl.
CPC ............ G21K 1/025 (2013.01); A61B 6/4291 (2013.01); G21K 1/10 (2013.01)

(58) Field of Classification Search
None
See application file for complete search history.

(56) References Cited

U.S. PATENT DOCUMENTS

| 4,220,890 A | 9/1980 | Beekmans |
| 4,340,818 A | 7/1982 | Barnes |
| 4,788,429 A | 11/1988 | Wilson |
| 5,099,859 A | 3/1992 | Bell |
| 5,557,650 A | 9/1996 | Guida et al. |
| 5,581,592 A | 12/1996 | Zarnoch et al. |
| 5,606,589 A | 2/1997 | Pellegrino et al. |
| 5,729,585 A | 3/1998 | Pellegrino et al. |
| 5,814,235 A | 9/1998 | Pellegrino et al. |
| 6,075,840 A | 6/2000 | Pellegrino et al. |

(Continued)

FOREIGN PATENT DOCUMENTS

| GB | 662046 A | 11/1951 |
| JP | 2008232731 A | 10/2008 |
| JP | 2011135934 A | 7/2011 |

OTHER PUBLICATIONS

Altunbas, Cem, "A dedicated two dimensional antiscatter grid for CBCT in radiation therapy", National Institutes of Health; University of Colorado Denver, Accessed Jul. 3, 2019, 4 pages.

(Continued)

*Primary Examiner* — Hoon K Song
(74) *Attorney, Agent, or Firm* — Dorsey & Whitney LLP

(57) ABSTRACT

Apparatus and methods are described for use with an X-ray system including an X-ray anti-scatter grid that includes at least a first layer of elongate radiopaque septa arranged such that longitudinal axes of each the septa belonging to the first layer are disposed along a first direction, in parallel to each other. Spaces between the septa are filled with air, and a rigid frame supports the septa. Two or more slotted plates are coupled to the rigid frame, each of the slotted plates defining a plurality of slots, each of the septa passing through a respective pair of slots defined by a pair of the slotted plates disposed on opposite sides of the frame from each other, such that the orientation of each of the septa with respect to the frame is determined by the orientation of the corresponding pair of slots with respect to the frame.

31 Claims, 9 Drawing Sheets

(56) References Cited

U.S. PATENT DOCUMENTS

| | | | |
|---|---|---|---|
| 6,177,237 B1 | 1/2001 | Guida et al. | |
| 6,438,210 B1 | 8/2002 | Castleberry | |
| 6,470,072 B1 | 10/2002 | Johnson | |
| 6,529,582 B2 | 3/2003 | Feldmesser et al. | |
| 6,690,767 B2 | 2/2004 | Davis | |
| 6,707,884 B1 * | 3/2004 | Ogawa | G21K 1/025 378/154 |
| 6,733,266 B1 | 5/2004 | Guida et al. | |
| 6,744,852 B2 | 6/2004 | Klotz et al. | |
| 6,778,632 B2 | 8/2004 | Hoheisel et al. | |
| 6,801,600 B2 | 10/2004 | Kohda | |
| 6,894,281 B2 | 5/2005 | Such et al. | |
| 6,951,628 B2 | 10/2005 | Eidam et al. | |
| 7,072,446 B2 | 7/2006 | Dobbs et al. | |
| 7,310,411 B2 | 12/2007 | Tang et al. | |
| 7,336,767 B1 | 2/2008 | Le | |
| 7,352,887 B2 | 4/2008 | Besson | |
| 7,356,126 B2 | 4/2008 | Bacher et al. | |
| 7,359,488 B1 | 4/2008 | Sayag | |
| 7,362,849 B2 | 4/2008 | Short et al. | |
| 7,368,151 B2 | 5/2008 | Souchay et al. | |
| 7,430,281 B2 | 9/2008 | Klausz | |
| 7,479,638 B2 | 1/2009 | Dorscheid et al. | |
| 7,518,136 B2 | 4/2009 | Appleby et al. | |
| 7,742,561 B2 | 6/2010 | Ueki | |
| 2004/0251420 A1 | 12/2004 | Sun | |
| 2006/0023832 A1 * | 2/2006 | Edie | A61B 6/4028 378/7 |
| 2009/0238324 A1 | 9/2009 | Oikawa | |
| 2010/0135456 A1 | 6/2010 | Jing et al. | |
| 2010/0239072 A1 | 9/2010 | Kurochi | |
| 2011/0099790 A1 * | 5/2011 | Tonami | G21K 1/025 29/428 |
| 2011/0170670 A1 | 7/2011 | Kuwabara | |
| 2013/0272505 A1 * | 10/2013 | Beck | G21K 1/10 378/154 |
| 2015/0318066 A1 | 11/2015 | Beck | |

OTHER PUBLICATIONS

Mikro, "Computed Tomography", www.mikrosystems.com/applications/computed-tomography, Accessed Jul. 3, 2019, 2 pages.

Philips Healthcare Hoogerhuis Peter, "The next step in making CT components", Jan. 27, 2016, 17 pages.

\* cited by examiner

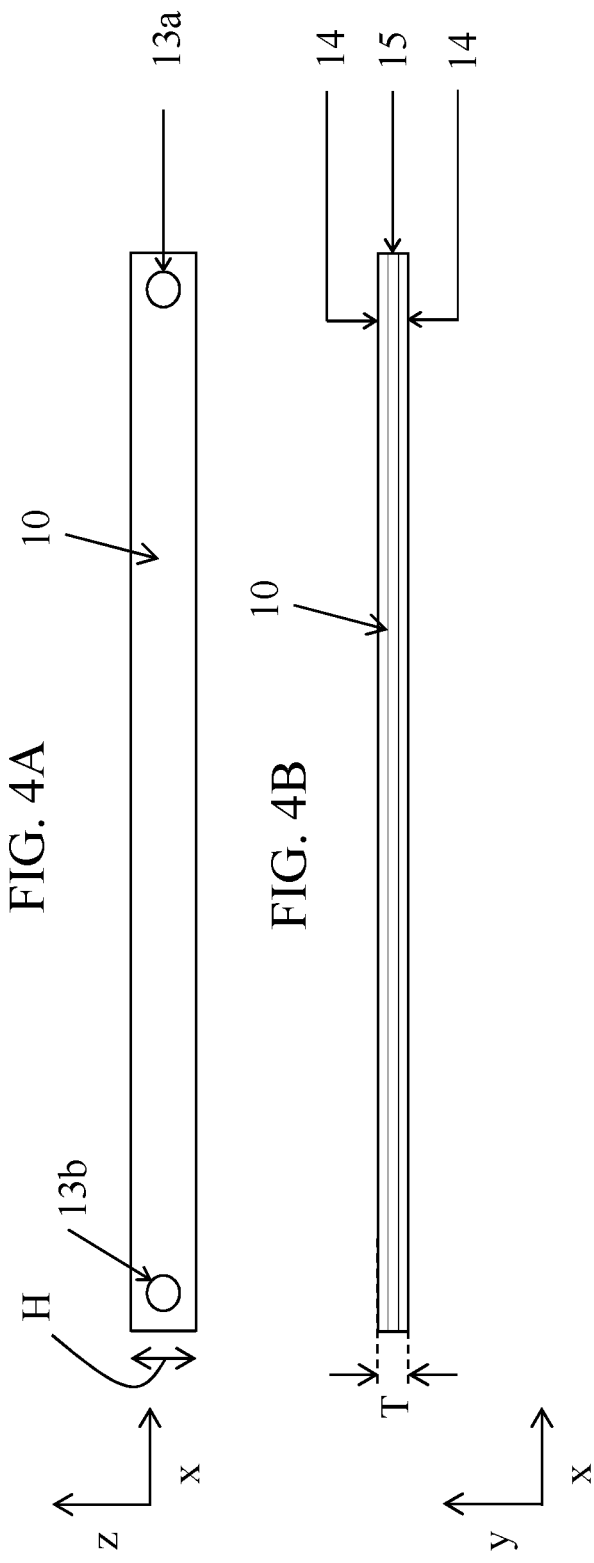

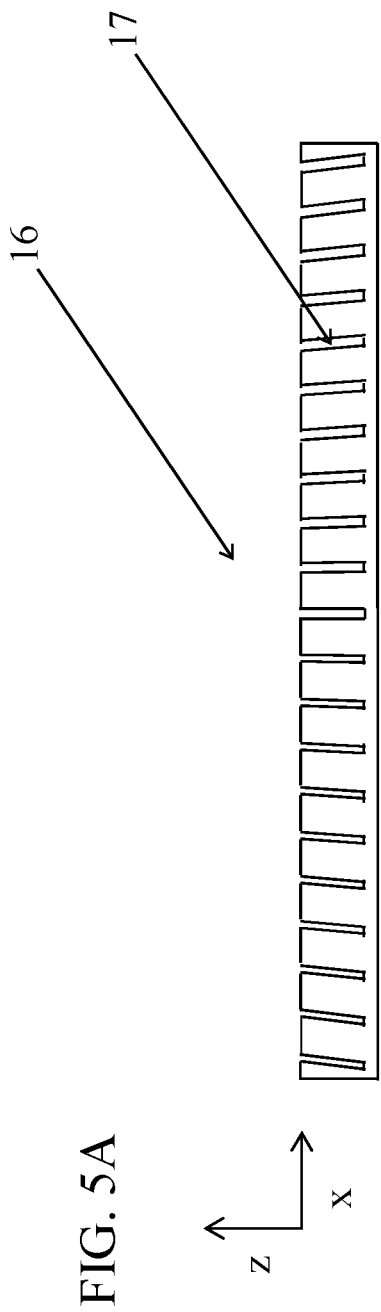
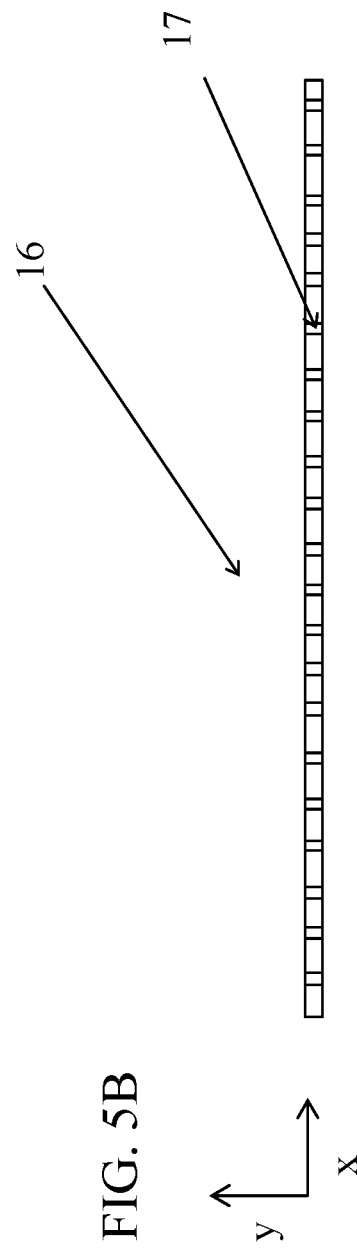
FIG. 5A
FIG. 5B

GRID FOR X-RAY IMAGING

FIELD OF EMBODIMENTS OF THE INVENTION

Applications of the present invention include an anti-scatter grid for use in medical projection X-ray imaging. More particularly, applications of the present invention relate to an air-filled anti-scatter grid for reducing the X-ray scatter radiation incident on the X-ray detector.

BACKGROUND

In transmission X-ray imaging, X-rays produced by an X-ray tube, penetrate an object and are then absorbed in an X-ray detector, leading to the creation of the X-ray image. X-rays that penetrate the object without interacting with the object (these rays travel on a straight-line path from the tube to the detector) are called primary X-rays. X-rays that penetrate the object after interacting with the object (and have been diverted from the original straight line path) are called scattered X-rays. Primary X-rays absorbed by the X-ray detector produce the primary image. Scattered X-rays absorbed by the X-ray detector produce the scatter image. The primary and scatter X-ray images are superimposed on each other and together produce the X-ray image. The primary image contains all the information of the X-ray image. The scatter image does not contain any useful information and reduces the signal-to-ratio (SNR) of the X-ray image. Therefore, for maximum SNR in the X-ray image, it is desired to reduce the number of scattered X-rays absorbed in the X-ray detector to a minimum while simultaneously preserving the number of primary X-rays absorbed in the X-ray detector.

Grids reduce the number of scattered X-rays absorbed in the X-ray detector. Grids also reduce the number of primary X-rays absorbed in the X-ray detector. Two performance metrics of grids are scattered X-ray transmission (Ts) and primary X-ray transmission (Tp). The measurement of these 2 metrics is described in the IEC document 60627: Diagnostic X-ray imaging equipment—Characteristics of general purpose and mammographic anti-scatter grids. An ideal grid has: Tp=1 and Ts=0. Typically, commercial grids have: Tp in the range of 0.6 to 0.8, and Ts in the range of 0.07 to 0.2. As a result of the transmitted scattered radiation and the reduction in the primary radiation, the SNR of the X-ray image is reduced by a factor of (versus an ideal grid):

SQRT[Tp/(1+SPR(Ts/Tp))], where SPR is the ratio of the number of scattered X-rays to the number of primary X-rays incident on the X-ray detector without any grid.

In projection X-ray imaging of the abdomen of adult humans the SPR is approximately 10. For abdominal imaging, with grid parameters: Tp=0.7 and Ts=0.1, the reduction in the image SNR is a factor of 0.55.

Medical projection X-ray imaging is performed with an X-ray tube having a 'point source' with produces a divergent x-ray beam. Due to the divergent beam geometry, grids have a 'focused geometry' and are called focused grids. Grid septa are configured so that the orientation of the height dimension of the grid septa is parallel to the direction of the primary X-rays. This configuration maximizes the transmission of the primary X-rays.

Reference is now made to FIGS. 1A and 1B, which are schematic illustrations of, respectively, a side view and a top view of a prior art X-ray grid. As shown in FIGS. 1A and 1B, prior art grids typically have septa 2 and interspace material 1. The septa are thin foils of high atomic number material (such as lead). The interspace material is low atomic number material (such as, aluminum) and fills the space between the septa. Typically, such prior art grids require a solid material to be used as the interspace material, because the septa are thin and require the support of the solid interspace material in order to maintain their shapes.

Reference is also made to FIG. 2, which is a schematic illustration of a side view of a projection imaging configuration, in accordance with prior art techniques. An X-ray tube 3 contains an X-ray focal spot 4, which emits all the primary X-rays used in projection imaging.

A first primary X-ray 5 is emitted from the focal spot, transverses the patient 7 and grid 8 and is absorbed in the X-ray detector 8a. A second primary X-ray 5a interacts with the patient 7 at point 5b. A scattered X-ray 6 is emitted from the interaction point and is absorbed in the grid septa at point 5c.

The function of the septa is to absorb the scattered X-rays. The grid is placed in the X-ray beam so that the septa are parallel to the direction of the primary X-rays. In order to preferentially absorb scattered X-rays and transmit primary X-rays the septa are typically thin foils, placed parallel to the direction of the primary X-rays (in order to minimize primary X-ray absorption), and made from high density, high atomic number material (in order to maximize scattered X-ray absorption).

SUMMARY OF EMBODIMENTS

In accordance with some applications of the present invention, an X-ray anti-scatter grid for use with an X-ray system includes at least a first layer of elongate radiopaque septa arranged such that longitudinal axes of each the septa belonging to the first layer are disposed along a first direction, in parallel to each other, spaces between the septa of the layer being filled with air. The elongate septa are coupled to a rigid frame, such that the rigid frame supports the elongate septa. Typically, the rigid frame and the elongate septa are not formed as an integral unit, for example, via a three-dimensional printing process. For some applications, two or more slotted plates are coupled to the rigid frame, with each of the slotted plates defining a plurality of slots. Each of the septa typically passes through a respective pair of slots defined by a pair of the slotted plates disposed on opposite sides of the frame from each other, such that an orientation of each of the septa with respect to the frame is determined by an orientation of the corresponding pair of slots with respect to the frame.

For some applications, the X-ray anti-scatter grid includes a second layer of elongate radiopaque septa, arranged such that longitudinal axes of each the septa belonging to the second layer are disposed along a second direction, in parallel to each other. The second direction is typically perpendicular to the first direction, such that, when viewed along a third direction that is perpendicular to the first and second directions, the first and second layers of radiopaque septa define a grid.

For some applications, a controller receives an input indicating a focal length of the X-ray system, and, in response thereto, the controller adjusts orientations of the septa within the first layer. For some applications, the controller adjusts orientations of the septa within the first layer by adjusting orientations of the slotted plates with respect to the frame, e.g., using a stepper motor.

There is therefore provided, in accordance with some applications of the present invention, apparatus for use with an X-ray system including:
an X-ray anti-scatter grid including:
at least a first layer of elongate radiopaque septa arranged such that longitudinal axes of each the septa belonging to the first layer are disposed along a first direction, in parallel to each other, spaces between the septa of the layer being filled with air;
a rigid frame configured to support the elongate septa; and
two or more slotted plates coupled to the rigid frame, each of the slotted plates defining a plurality of slots, each of the septa passing through a respective pair of slots defined by a pair of the slotted plates disposed on opposite sides of the frame from each other, such that an orientation of each of the septa with respect to the frame is determined by an orientation of the corresponding pair of slots with respect to the frame.

In some applications, the rigid frame and the elongate septa are not formed as an integral unit. In some applications, the rigid frame and the elongate septa are not formed via a three-dimensional printing process.

In some applications, the X-ray anti-scatter grid includes a single layer of elongate radiopaque septa. In some applications, the X-ray anti-scatter grid further includes a second layer of elongate radiopaque septa, arranged such that longitudinal axes of each the septa belonging to the second layer are disposed along a second direction, in parallel to each other, the second direction being perpendicular to the first direction, such that, when viewed along a third direction that is perpendicular to the first and second directions, the first and second layers of radiopaque septa define a grid.

In some applications, a thickness of each of the septa is between 0.04 mm and 0.1 mm. In some applications, a height of each of the septa is between 10 mm and 20 mm. In some applications, within the layer of septa, a distance between each of the septa and adjacent septa is between 0.5 mm and 1.5 mm.

In some applications, the apparatus further includes a controller configured to:
receive an input indicating a focal length of the X-ray system, and
in response thereto, to adjust orientations of the septa within the first layer.

In some applications, the controller is configured to adjust orientations of the septa within the first layer such that the septa are parallel to a primary X-ray beam generated by the X-ray system.

In some applications, the X-ray system includes an X-ray system processor, and wherein the controller is configured to automatically receive the input indicating the focal length of the X-ray system from the X-ray system processor. In some applications, the controller is configured to manually receive the input indicating the focal length of the X-ray system. In some applications, the controller is configured to adjust orientations of the septa within the first layer by adjusting orientations of the slotted plates with respect to the frame. In some applications, the apparatus further includes one or more stepper motors, and the controller is configured to adjust orientations of the septa within the first layer by adjusting orientations of the slotted plates with respect to the frame using the stepper motor.

In some applications, each of the septa includes a foil core that is coated with a metal that has an atomic number that is greater than an atomic number of the foil core. In some applications, the foil core includes a copper foil core. In some applications, the metal coating includes tin.

There is further provided, in accordance with some applications of the present invention, a method including:
driving an X-ray system to direct X-rays from an X-ray source to an X-ray detector; and
directing the X-rays via an X-ray anti-scatter grid that includes:
at least a first layer of elongate radiopaque septa arranged such that longitudinal axes of each the septa belonging to the first layer are disposed along a first direction, in parallel to each other, spaces between the septa of the layer being filled with air;
a rigid frame configured to support the elongate septa; and
two or more slotted plates coupled to the rigid frame, each of the slotted plates defining a plurality of slots, each of the septa passing through a respective pair of slots defined by a pair of the slotted plates disposed on opposite sides of the frame from each other, such that an orientation of each of the septa with respect to the frame is determined by an orientation of the corresponding pair of slots with respect to the frame.

There is further provided, in accordance with some applications of the present invention, apparatus for use with an X-ray system including:
an X-ray anti-scatter grid comprising:
at least a first layer of elongate radiopaque septa that comprises a plurality of elongate radiopaque septa arranged such that longitudinal axes of each the septa belonging to the first layer are disposed along a first direction, in parallel to each other, spaces between the septa of the layer being filled with air; and
a controller configured to:
receive an input indicating a focal length of the X-ray system, and
in response thereto, to adjust orientations of the septa within the layer.

In some applications, the controller is configured to adjust orientations of the septa within the first layer such that the septa are parallel to a primary X-ray beam generated by the X-ray system.

In some applications, wherein the X-ray system includes an X-ray system processor, and wherein the controller is configured to automatically receive the input indicating the focal length of the X-ray system from the X-ray system processor.

In some applications, wherein the controller is configured to manually receive the input indicating the focal length of the X-ray system.

In some applications, wherein the X-ray anti-scatter grid includes a single layer of elongate radiopaque septa.

In some applications, the X-ray anti-scatter grid further includes a second layer of elongate radiopaque septa, arranged such that longitudinal axes of each the septa belonging to the second layer are disposed along a second direction, in parallel to each other, the second direction being perpendicular to the first direction, such that, when viewed along a third direction that is perpendicular to the first and second directions, the first and second layers of radiopaque septa define a grid.

In some applications, a thickness of each of the septa is between 0.04 mm and 0.1 mm. In some applications, a height of each of the septa is between 10 mm and 20 mm. In some applications, within the layer of septa, a distance between each of the septa and adjacent septa is between 0.5 mm and 1.5 mm.

In some applications, the X-ray anti-scatter grid further includes:
a rigid frame configured to support the elongate septa; and two or more slotted plates coupled to the rigid frame, each of the slotted plates defining a plurality of slots, each of the septa passing through a respective pair of slots defined by the plates, such that an orientation of each of the septa with respect to the frame is determined by an orientation of the corresponding pair of slots with respect to the frame.

In some applications, the controller is configured to adjust orientations of the septa within the first layer by adjusting orientations of the slotted plates with respect to the frame. In some applications, the apparatus further includes one or more stepper motors, and the controller is configured to adjust orientations of the septa within the first layer by adjusting orientations of the slotted plates with respect to the frame using the stepper motor.

In some applications, each of the septa includes a foil core that is coated with a metal that has an atomic number that is greater than an atomic number of the foil core. In some applications, the foil core includes a copper foil core. In some applications, the metal coating includes tin.

There is further provided, in accordance with some applications of the present invention, a method for use with an X-ray system that is configured to direct X-rays from an X-ray source to an X-ray detector, the method including:

directing the X-rays via an X-ray anti-scatter grid that include at least a first layer of elongate radiopaque septa that comprises a plurality of elongate radiopaque septa arranged such that longitudinal axes of each the septa belonging to the first layer are disposed along a first direction, in parallel to each other, spaces between the septa of the layer being filled with air; and in response to an indication of a focal length of the X-ray system, causing orientations of the septa within the layer to be adjusted.

There is further provided, in accordance with some applications of the present invention, apparatus for use with an X-ray system including:

an X-ray anti-scatter grid comprising:
at least a first layer of elongate radiopaque septa arranged such that longitudinal axes of each the septa belonging to the first layer are disposed along a first direction, in parallel to each other, spaces between the septa of the layer being filled with air;
a rigid frame to which the elongate septa are coupled, such that the rigid frame supports the elongate septa, the rigid frame and the elongate septa not being formed as an integral unit.

There is further provided, in accordance with some applications of the present invention, apparatus for use with an X-ray system including:

an X-ray anti-scatter grid comprising:
at least a first layer of elongate radiopaque septa arranged such that longitudinal axes of each the septa belonging to the first layer are disposed along a first direction, in parallel to each other, spaces between the septa of the layer being filled with air;
a rigid frame to which the elongate septa are coupled, such that the rigid frame supports the elongate septa, the rigid frame and the elongate septa not being formed via a three-dimensional printing process.

The present invention will be more fully understood from the following detailed description of embodiments thereof, taken together with the drawings, in which:

BRIEF DESCRIPTION OF THE DRAWINGS

FIGS. 4A and 4B are schematic illustrations of, respectively, a side view and top view of the septa of a grid, in accordance with some applications of the present invention;

FIGS. 5A and 5B are schematic illustrations of, respectively, a side view and top view of a slotted plate, in accordance with some applications of the present invention;

DETAILED DESCRIPTION OF EMBODIMENTS

Figure 1A:
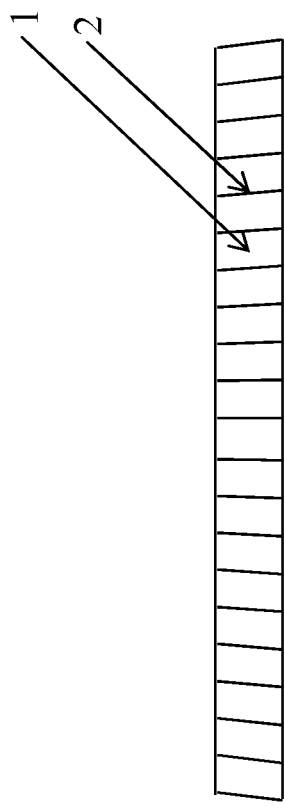
FIGS. 1A and 1B are schematic illustrations of a side view and top view of a focused grid with interspace material and septa, in accordance with prior art techniques.
Figure 1B:
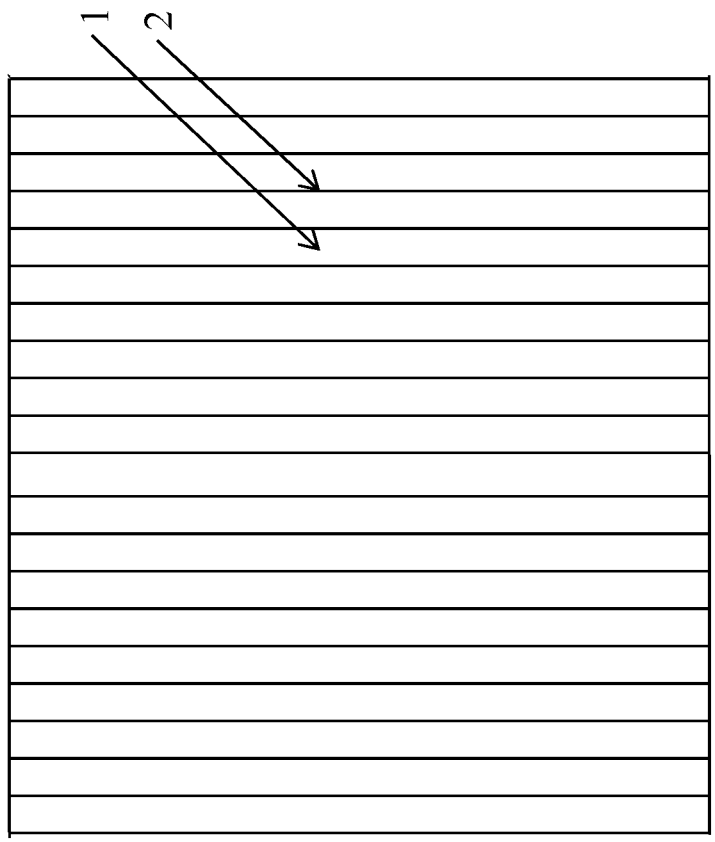
Figure 2:
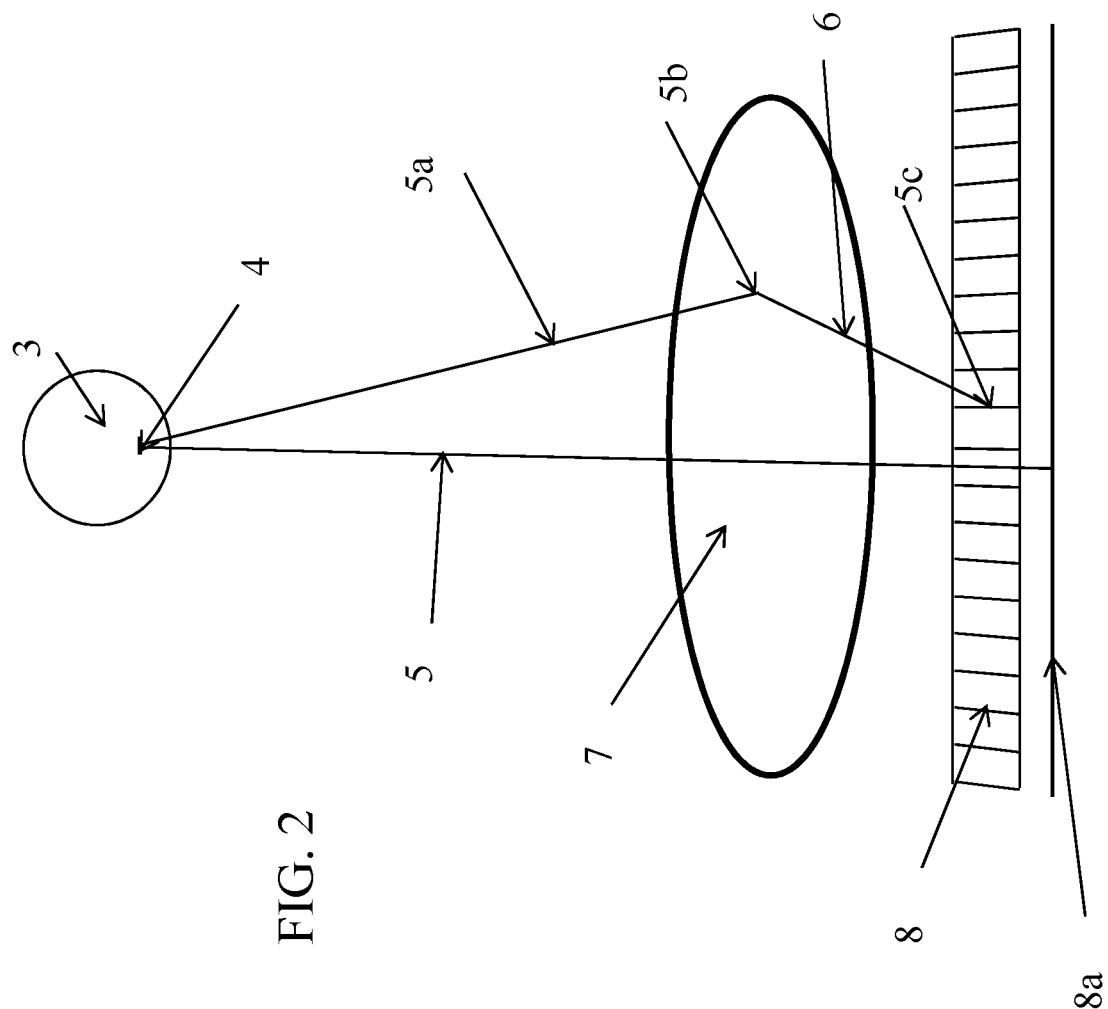
FIG. 2 is a schematic illustration of a side view of a projection imaging configuration, in accordance with prior art techniques.
Figure 3A:
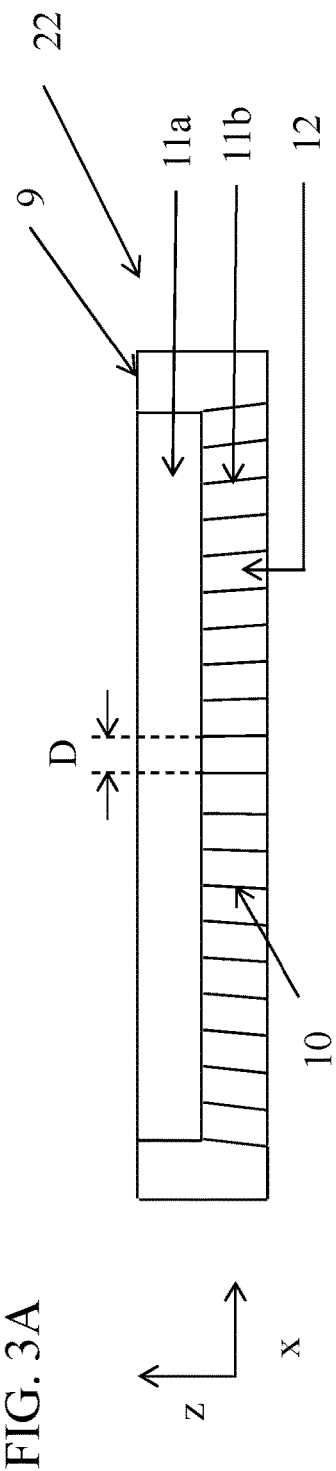
FIGS. 3A and 3B are schematic illustrations of, respectively, a side view and a top view of a grid, in accordance with some applications of the present invention.
Figure 3B:
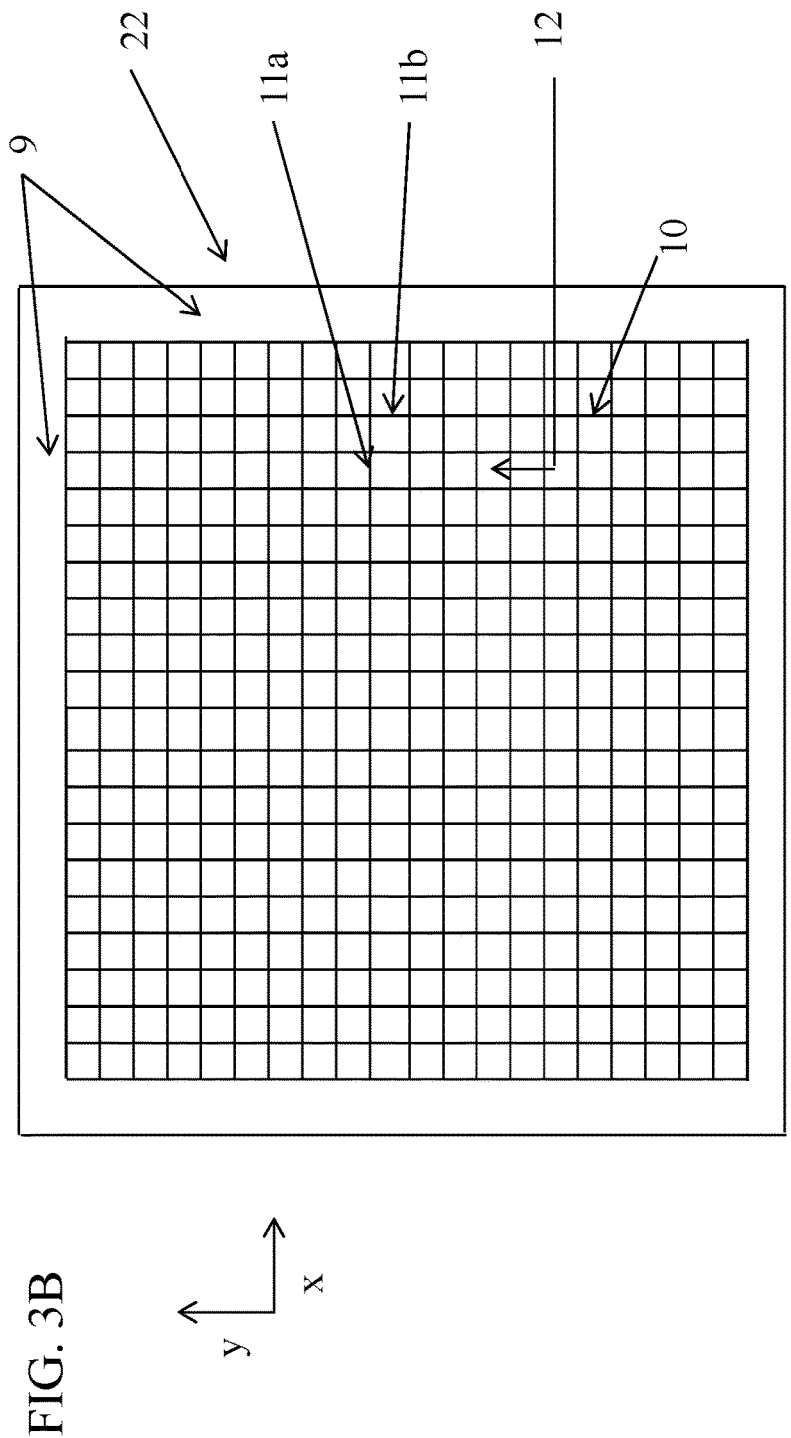

Reference is now made to FIGS. 3A and 3B, which are schematic illustrations of a grid 22, in accordance with some applications of the present invention. FIG. 3A shows a side view of the grid (looking along the y-direction), and FIG. 3B shows a top view of the grid (looking along the z-direction). For some applications, grid 22 includes first and second layers of elongate radiopaque septa 10, e.g., top layer 11a (closer to the X-ray focal spot) and bottom layer 11b. The first layer of elongate radiopaque septa includes a plurality of elongate radiopaque septa 10 arranged such that longitudinal axes of each the septa belonging to the first layer are disposed along a first direction (e.g., the x-direction), in parallel to each other. The second layer of elongate radiopaque septa includes a plurality of elongate radiopaque septa 10 arranged such that longitudinal axes of each the septa belonging to the second layer are disposed along a second direction, in parallel to each other, the second direction being generally perpendicular to the first direction (e.g., the y-direction). The first layer of radiopaque septa are disposed above the second layer of radiopaque septa, such that, when viewed along a third direction that is perpendicular to the first and second directions (e.g., the z-direction), the first and second layers of radiopaque septa define a grid. The septa are maintained in their respective positions within grid 22 by a rigid frame 9 that is disposed around the outside of the grid and supports the ends of the septa. It is noted that the frame and the septa are typically separate components that are coupled to each other, and are not made of a single integral structure (e.g., via a 3D printing process). The interspace material 12 (i.e., the spaces between the septa of each of the layers) is typically air. For some applications, within each of the layers of septa, a distance D (shown in FIG. 3A) between each of the septa and adjacent septa (also known as the "pitch" of the grid) is between 0.5 mm and 1.5 mm.

Each layer of septa is a linear, focused air-filled grid. The two layers are disposed such that, together, they form a crisscross grid. As shown in FIG. 3B, the septa of the two layers (top layer 11a and bottom layer 11b) are perpendicular to each other.

Reference is now made to FIGS. 4A-B, which show the structure of an individual septum 10, in accordance with some applications of the present invention. FIG. 4A shows a side view of a septum (looking along the y-direction), and FIG. 4B shows a top view of the septum (looking along the z-direction). The septa are typically made of a core 15 and a coating 14 that coats the core. Typically, the core provides rigidity to the septa and the coating provides X-ray absorption. For some applications, the core is a foil core and the coating is a metal that has an atomic number that is greater than the atomic number of the foil core. For example, the core may be copper and/or steel, and the coating may be tin. For some applications, the septa are made of tungsten and/or phosphor bronze. For example, all of the septa may be made of either tungsten or phosphor bronze. Alternatively, septa made of tungsten and septa made of phosphor bronze may be alternated with one another (e.g., such that odd-numbered septa are made of tungsten and even-numbered septa are made of phosphor bronze, or vice versa), or used with each other in a different combination. Typically, for applications in which the septa are made of tungsten and/or phosphor bronze, the septa are not constructed using separate materials for cores and coatings of the septa. Rather, each of the septa is typically made of either one or the other of these materials.

Typically, the septa define holes 13a and 13b in the ends of the septa for connection to rods, as described hereinbelow. For some applications, the rods are circular, and holes 13a and 13b are circular (as shown) to conform with the circular rods.

For some applications, a thickness T of each of the septa 10 is greater than 0.04 mm and/or less than 0.1 mm, e.g., between 0.04 mm and 0.1 mm. For some applications, a height H of each of the septa is greater than 10 mm and/or less than 20 mm, e.g., between 10 mm and 20 mm.

Reference is now made to FIGS. 5A and 5B, which are schematic illustrations of respective views of a slotted plate 16, in accordance with some applications of the present invention. FIG. 5A shows a side view of the plate (looking along the y-direction), and FIG. 5B shows a top view of the plate (looking along the z-direction). For some applications, the septa are held in place, at each end, by the slots 17 defined by the slotted plates. The distance between the septa and the orientation of the septa in the grid is set by slots in the slotted plates. The width of the slots is typically slightly larger than the thickness of the septa. The slotted plates typically are coupled to rigid frame 9. Typically, each of the septa passes through a respective pair of slots, such that an orientation of each of the septa with respect to the frame is determined by an orientation of the corresponding pair of slots with respect to the frame.

Figure 6:
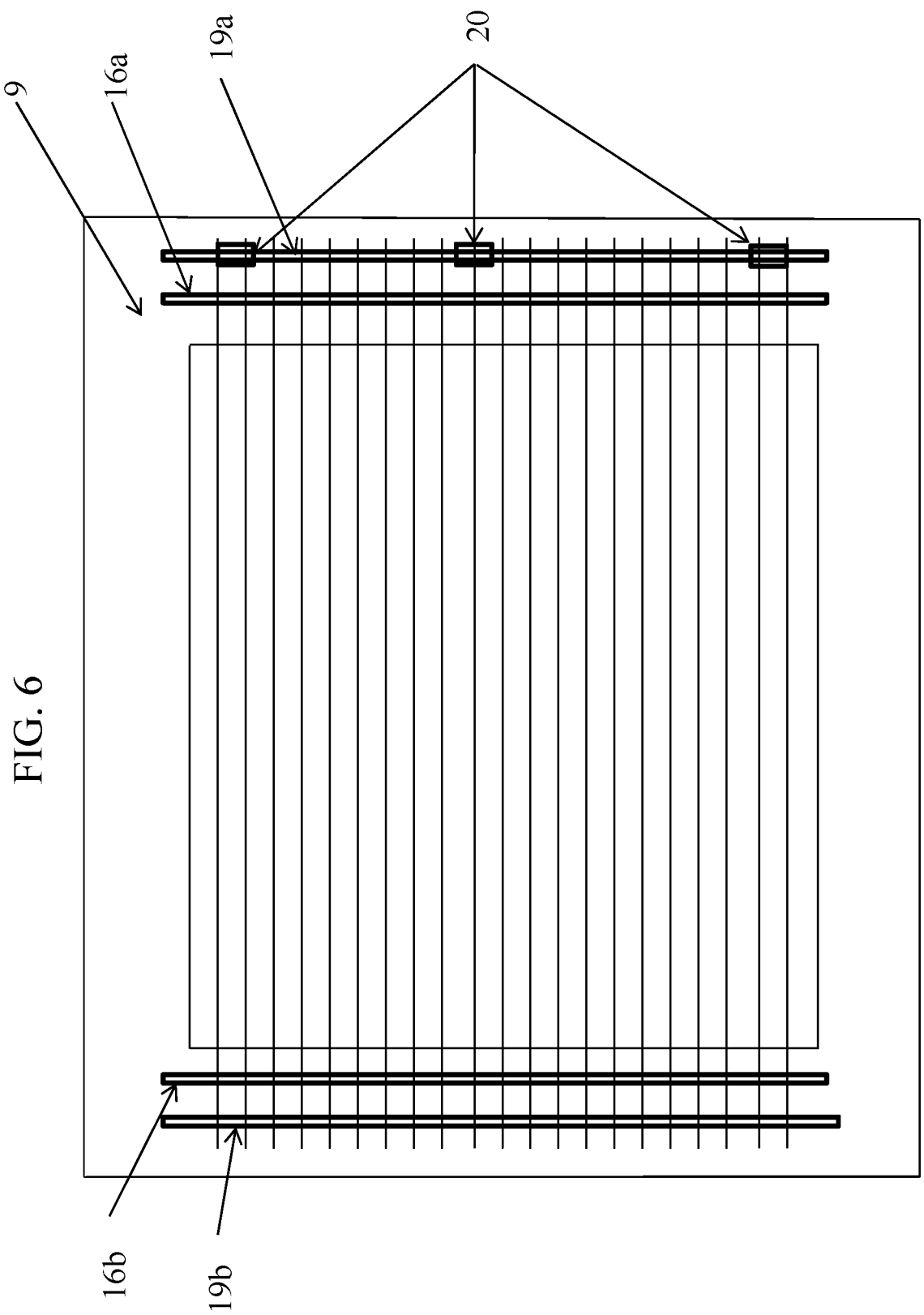
FIG. 6 is a schematic illustration of a top view of a grid including septa and a frame, in accordance with some applications of the present invention.

Reference is now made to FIG. 6, which is a schematic illustration of septa 10 from one layer being maintained in position by rigid frame 9, in accordance with some applications of the present invention. As described hereinabove, for some applications, the septa are held in place, at each end, by the slots defined by slotted plates 16a, 16b that are disposed on rigid frame 9. The ends of the septa are attached to rods 19a, 19b, for example, via holes in the ends of the septa, as shown in FIG. 4A. For some applications, the rods are circular. Typically, the rods are disposed upon frame 9. One of the rods (e.g., rod 19a) is moved away from the second rod (e.g., rod 19b) so that the septa are tightly stretched between the rods. For some applications, a pulling mechanism 20 is disposed upon frame 9 and the rod is pulled using the pulling mechanism.

It is noted that grid 22 as shown in FIGS. 3A-6 is configured such that (a) the septa are supported in their positions by elements that are disposed on rigid frame 9 (e.g., slotted plates 16a, 16b as described hereinabove), and (b) between the support elements that are disposed upon the rigid frame the septa have a sufficient amount of rigidity to support themselves (e.g., by virtue of the fact that the septa are constructed from a core and a coating, as described hereinabove). Typically, the grid is configured, such that when the grid is used in X-ray imaging, the frame itself is not within the field of view of the X-ray detector. As such, all of the support elements that support the septa in place are disposed outside of the field of view of the X-ray detector, and do not absorb any X-rays.

As described hereinabove, typically within each of the layers of septa, spaces between the septa are filled with air. For some applications, this provides an advantage over conventional grids (in which a low atomic number solid material (such as aluminum) is typically used as the interspace material, as described hereinabove), because air does not absorb any X-rays whereas the interspace material that is used in conventional grids typically does absorb some X-rays. Moreover, since the interspace material on conventional grids absorbs X-rays, this typically places an upper limit on the heights of the septa that may be used in the grid. By contrast, since the interspace material in grid 22 is air, grid 22 is not limited in this manner. Therefore, typically, the height H of each of the septa is greater than 10 mm and/or less than 20 mm, e.g., between 10 mm and 20 mm. In turn, for some applications, by virtue of septa having the aforementioned heights, the distance D (shown in FIG. 3A) between each of the septa and adjacent septa (also known as the "pitch" of the grid) may be between 0.5 mm and 1.5 mm, and the grid may still have a grid ratio of more than 10, or more than 15 (grid ratio being defined as the ratio of the heights of the septa to the pitch of the grid, i.e., H:D). Since conventional grids typically have an upper limit on the height of the septa, e.g., for the reasons provided hereinabove, it is typically the case that there is a corresponding upper limit on the pitch of the grid, in order to provide such a grid ratio.

Although the grid shown in FIGS. 3A-6 shows two layers of septa that are disposed perpendicularly with respect to each other such as to form a grid, for some applications, grid 22 is configured as described herein, but includes only a single layer of septa, the longitudinal axes of which are parallel to each other. Typically, such a grid would include either layer 11a or 11b of septa. Typically, for such applications, the height H of each of the septa is still greater than 10 mm and/or less than 20 mm, e.g., between 10 mm and 20 mm. In all other aspects, such a grid would be generally similar to that described hereinabove.

Figure 7:
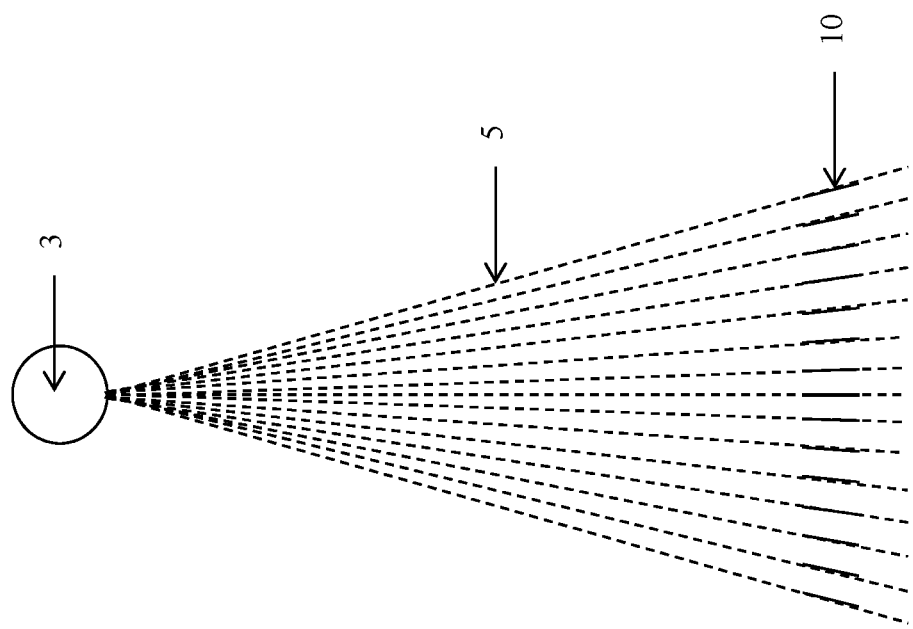
FIG. 7 is a schematic illustration of a grid of septa placed in an X-ray beam and oriented such that the septa are parallel to the direction of the primary X-ray beams, in accordance with some applications of the present invention.

Reference is now made to FIG. 7, which is a schematic illustration of a grid 22 of septa 10 placed in an X-ray beam and oriented such that the septa are parallel to the direction of the primary X-ray beams 5, in accordance with some applications of the present invention. As shown, typically, the X-ray beam spreads in a fan, such that the primary X-ray beams are disposed at respective angles to the axis of X-ray source 3. Typically, conventional grids are suitable for use with a specific focal spot-detector length (i.e., focal length). If a focused grid is used in an imaging examination does not correspond to the focal length of the grid, primary beam cut-off occurs where the transmission of the primary beam is reduced and thus the performance of the grid is degraded.

However, diagnostic X-ray systems typically perform X-ray examinations at different focal lengths. When a fixed focal length grid is used with X-ray examinations of different focal lengths, the grid performance is degraded. Conversely, if different X-ray examinations at different focal lengths utilize multiple grids (with different focal lengths), this requires an operator to manually change the grids for the different X-ray examinations. Therefore, in accordance with some applications of the present invention, grid 22 is configured such as to be adjustable such as to operate at multiple focal lengths.

For some applications, the orientation of the grid septa are adjustable such that the grid is configured to operate at multiple focal lengths. Typically, such applications are applicable to a grid that includes two layers of septa as described hereinabove, or to a grid that includes only a single layer of septa.

Figure 8:
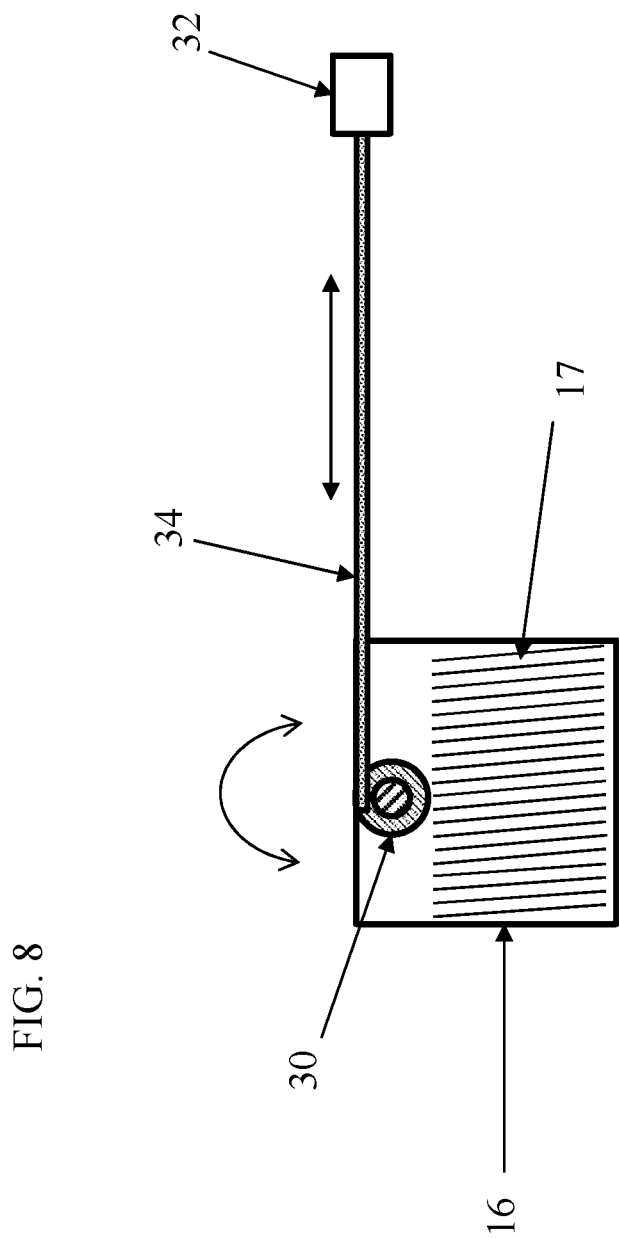
FIG. 8 is a schematic illustration of a slotted plate mounted on a rotation axis, in accordance with some applications of the present invention.

Reference is now made to FIG. 8, which is a schematic illustration of slotted plate 16 (e.g., slotted plate 16a or slotted plate 16b, described hereinabove) mounted on a rotation axis 30, in accordance with some applications of the present invention. For some applications, an actuator 32 is used to mechanically adjust the orientation of the septa. For example, the actuator may be a stepper motor that is coupled to the septa via a gear drive 34. Typically, the orientation of the septa is determined by the orientations of slots 17 in slotted-plates 16 (described hereinabove with reference to FIGS. 5A and 5B), and by the orientations of the slotted plates. For some applications, each of the septa is held within slots of a pair of slotted plates, the slotted plates being disposed at respective ends of the septum. Typically, the angle of the septum with respect to the slotted plates (and therefore the angles of the septa with respect to the frame) is fixed by the orientations of the corresponding pair of slots 17 in the pair of slotted-plates 16. For some applications, the orientations of the slotted plates is controlled by actuator 32. For some applications, the range of the rotation motion of the slotted plates is up to +/−5 degrees from a central position of the slotted plates. The rotation of the slotted plates typically results in a rotation of the orientation of the septa which adjusts the focal length of the grid.

Figure 9:
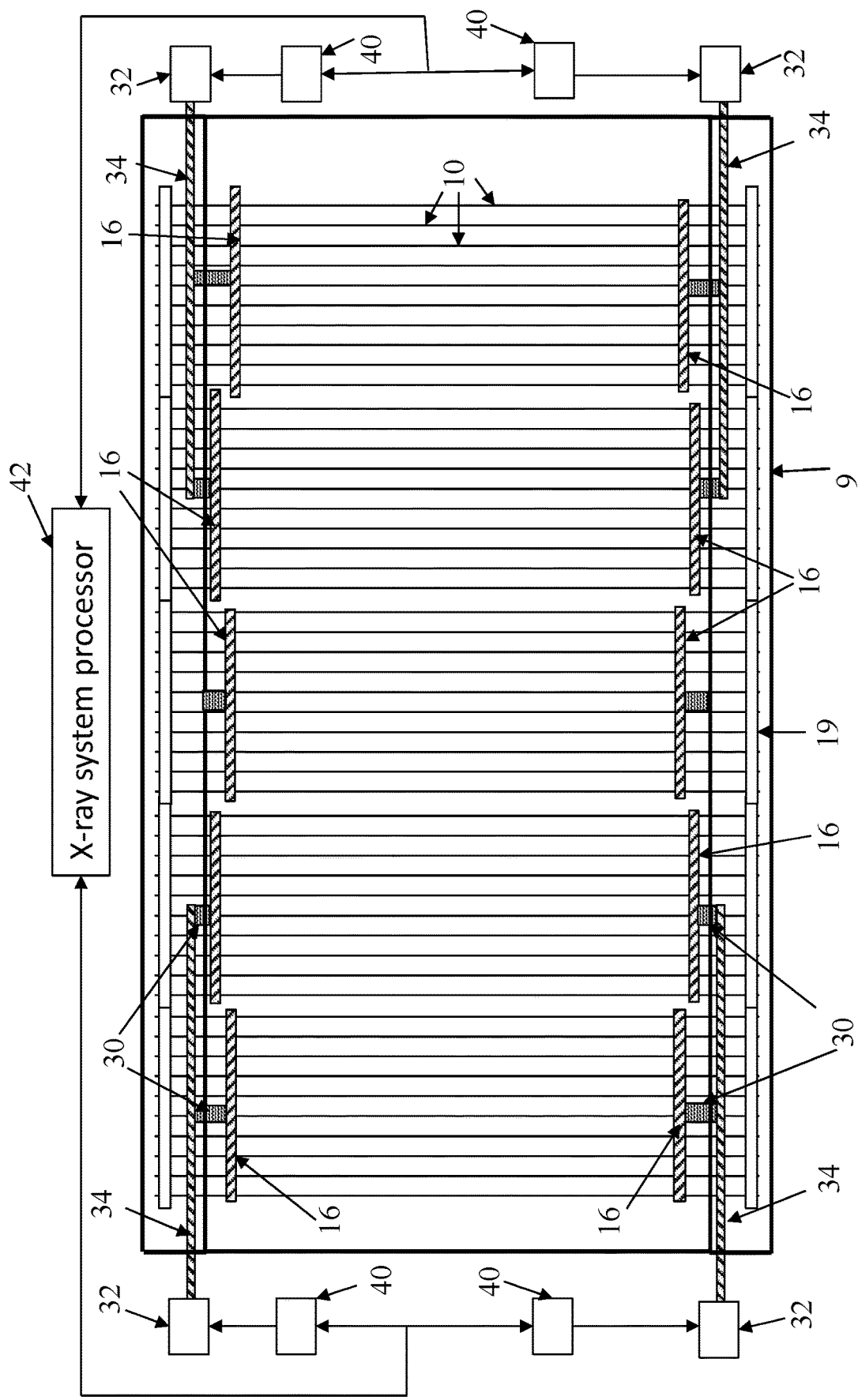
FIG. 9 is a schematic illustration of a grid that is configured to operate at multiple focal lengths, in accordance with some applications of the present invention.

Reference is now made to FIG. 9, which is a schematic illustration of grid 22, grid 22 being configured to operate at multiple focal lengths, in accordance with some applications of the present invention. For some applications, grid 22 includes multiple groups of septa 10 aligned adjacent to each other to cover the entire field of view of the x-ray beam. For some applications, an electronic controller 40 (e.g., circuitry and a processor) is configured to receive focal length inputs from an X-ray system processor 42. Typically, in response thereto, the electronic controller drives actuators 32 that are associated with respective of slotted plates 16 to adjust the orientations of the slotted plates, such that each group of septa is oriented in an orientation that is suitable for the received focal length inputs. This method of automatically changing the orientation of the grid septa as described herein typically enables the use of the grid in X-ray examinations with different focal lengths without any need for operator intervention.

Typically, the slotted-plates 16 and the rods 19 are physically coupled to rigid frame 9, such that the frame provides mechanical stability for the slotted plates, the rods, and the septa. One or more motors (e.g., four motors, as shown in the X-ray system of FIG. 9) are typically used to drive the rotation of the slotted-plates. For some applications, each group of septa, held in place by a pair of slotted plates, is rotated to a respective different angle (depending on the position of the group of septa in the grid), such as to produce the required orientation for each group of septa as a function of the required focal length. Typically, the one or more motors are connected to the X-ray system processor (e.g., via controllers 40) and receive the focal length input information from the X-ray system for adjusting the orientation of the septa, to dynamically change the configuration of the variable focus grid in response to the input information. Typically, the motors are configured to drive the slotted plates to adjust their orientations by driving rotation axes 30 to rotate via gear drives 34. For some applications a single motor is configured to control more than one rotation axis, as shown in FIG. 9. For some applications, controllers 40 are configured to send an input to the X-ray system processor, e.g., to transmit a ready status to the X-ray system processor.

For some applications, generally similar techniques to those described with reference to FIG. 9 are performed, but a human operator (a) manually inputs the focal length of the X-ray system to controllers 40, and/or (b) manually instructs the X-ray system to acquire X-rays, once the grid has been correctly configured by controllers 40.

Applications of the invention described herein can take the form of a computer program product accessible from a computer-usable or computer-readable medium (e.g., a non-transitory computer-readable medium) providing program code for use by or in connection with a computer or any instruction execution system, such as controller 40 and/or X-ray system processor 42. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., controller 40 and/or X-ray system processor 42) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the applications of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., controller 40 and/or X-ray system processor 42) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Controller 40 and/or X-ray system processor 42 is typically a hardware device programmed with computer program instructions to produce a special purpose computer. For example, when programmed to perform the algorithms described with reference to the figures, controller 40 and/or X-ray system processor 42 typically acts as a special purpose X-ray-grid-controller computer processor. Typically, the operations described herein that are performed by controller 40 and/or X-ray system processor 42 transform the physical state of a memory, which is a real physical article, to have a different magnetic polarity, electrical charge, or the like depending on the technology of the memory that is used. For some applications, operations that are described as being performed by a computer processor are performed by a plurality of computer processors in combination with each other.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with an X-ray system comprising:
an X-ray anti-scatter grid comprising:
at least a first layer of elongate radiopaque septa arranged such that longitudinal axes of each the septa belonging to the first layer are disposed along a first direction, in parallel to each other, spaces between the septa of the layer being filled with air;
a rigid frame configured to support the elongate septa;
two or more slotted plates coupled to the rigid frame, each of the slotted plates defining a plurality of slots, each of the septa passing through a respective pair of slots defined by a pair of the slotted plates disposed on opposite sides of the frame from each other, such that an orientation of each of the septa with respect to the frame is determined by an orientation of the corresponding pair of slots with respect to the frame; and
a pulling mechanism disposed upon the frame, the pulling mechanism being configured to permanently apply tension to the plurality of septa that are arranged in parallel to each other, such that tension is applied to the plurality of septa by the pulling mechanism during use of the X-ray anti-scatter grid; and
a controller configured to:
receive an input indicating a focal length of the X-ray system, and
in response thereto, to adjust orientations of the septa within the first layer.

2. The apparatus according to claim 1, wherein the controller is configured to adjust orientations of the septa within the first layer such that the septa are parallel to a primary X-ray beam generated by the X-ray system.

3. The apparatus according to claim 1, wherein the X-ray system includes an X-ray system processor, and wherein the controller is configured to automatically receive the input indicating the focal length of the X-ray system from the X-ray system processor.

4. The apparatus according to claim 1, wherein the controller is configured to manually receive the input indicating the focal length of the X-ray system.

5. The apparatus according to claim 1, wherein the controller is configured to adjust orientations of the septa within the first layer by adjusting orientations of the slotted plates with respect to the frame.

6. The apparatus according to claim 5, further comprising one or more stepper motors, wherein the controller is configured to adjust orientations of the septa within the first layer by adjusting orientations of the slotted plates with respect to the frame using the stepper motor.

7. Apparatus for use with an X-ray system comprising:
an X-ray anti-scatter grid comprising:
at least a first layer of elongate radiopaque septa arranged such that longitudinal axes of each the septa belonging to the first layer are disposed along a first direction, in parallel to each other, spaces between the septa of the layer being filled with air;
a rigid frame configured to support the elongate septa;
two or more slotted plates coupled to the rigid frame, each of the slotted plates defining a plurality of slots, each of the septa passing through a respective pair of slots defined by a pair of the slotted plates disposed on opposite sides of the frame from each other, such that an orientation of each of the septa with respect to the frame is determined by an orientation of the corresponding pair of slots with respect to the frame; and
a pulling mechanism disposed upon the frame, the pulling mechanism being configured to permanently apply tension to the plurality of septa that are arranged in parallel to each other, such that tension is applied to the plurality of septa by the pulling mechanism during use of the X-ray anti-scatter grid,
wherein each of the septa comprises a foil core that is coated with a metal that has an atomic number that is greater than an atomic number of the foil core.

8. The apparatus according to claim 7, wherein the rigid frame and the elongate septa are not formed as an integral unit.

9. The apparatus according to claim 7, wherein the rigid frame and the elongate septa are not formed via a three-dimensional printing process.

10. The apparatus according to claim 7, wherein the X-ray anti-scatter grid comprises a single layer of elongate radiopaque septa.

11. The apparatus according to claim 7, wherein the X-ray anti-scatter grid further comprises a second layer of elongate radiopaque septa, arranged such that longitudinal axes of each the septa belonging to the second layer are disposed along a second direction, in parallel to each other, the second direction being perpendicular to the first direction, such that, when viewed along a third direction that is perpendicular to the first and second directions, the first and second layers of radiopaque septa define a grid.

12. The apparatus according to claim 7, wherein a thickness of each of the septa is between 0.04 mm and 0.1 mm.

13. The apparatus according to claim 7, wherein a height of each of the septa is between 10 mm and 20 mm.

14. The apparatus according to claim 7, wherein, within the layer of septa, a distance between each of the septa and adjacent septa is between 0.5 mm and 1.5 mm.

15. The apparatus according to claim 7, wherein the foil core comprises a copper foil core.

16. The apparatus according to claim 7, wherein the metal coating comprises tin.

17. The apparatus according to claim 7, wherein each of the septa comprises phosphor bronze.

18. A method comprising:
driving an X-ray system to direct X-rays from an X-ray source to an X-ray detector; and
directing the X-rays via an X-ray anti-scatter grid that includes:
at least a first layer of elongate radiopaque septa arranged such that longitudinal axes of each the septa belonging to the first layer are disposed along a first direction, in parallel to each other, spaces between the septa of the layer being filled with air;
a rigid frame configured to support the elongate septa;
two or more slotted plates coupled to the rigid frame, each of the slotted plates defining a plurality of slots, each of the septa passing through a respective pair of slots defined by a pair of the slotted plates disposed on opposite sides of the frame from each other, such that an orientation of each of the septa with respect to the frame is determined by an orientation of the corresponding pair of slots with respect to the frame, and
a pulling mechanism disposed upon the frame, the pulling mechanism being configured to permanently apply tension to the plurality of septa that are arranged in parallel to each other, such that tension is applied to the plurality of septa by the pulling mechanism while the X-ray system directs X-rays from an X-ray source to an X-ray detector; and
in response to an indication of a focal length of the X-ray system, causing orientations of the septa within the first layer to be adjusted.

19. The method according to claim 18, wherein causing orientations of the septa within the first layer to be adjusted comprises causing the orientations of the septa within the first layer to be parallel to a primary X-ray beam generated by the X-ray system.

20. The method according to claim 19, wherein causing orientations of the septa within the first layer to be adjusted comprises automatically causing orientations of the septa within the first layer to be adjusted in response to an input indicating the focal length of the X-ray system from the X-ray system processor.

21. The method according to claim 19, wherein causing orientations of the septa within the first layer to be adjusted comprises causing orientations of the septa within the first layer to be adjusted in response to a manual input indicating the focal length of the X-ray system.

22. The method according to claim 19, wherein causing orientations of the septa within the first layer to be adjusted comprises adjusting orientations of the slotted plates with respect to the frame.

23. The method according to claim 22, wherein causing orientations of the septa within the first layer to be adjusted comprises adjusting orientations of the slotted plates with respect to the frame using a stepper motor.

24. A method comprising:
driving an X-ray system to direct X-rays from an X-ray source to an X-ray detector; and
directing the X-rays via an X-ray anti-scatter grid that includes:
at least a first layer of elongate radiopaque septa arranged such that longitudinal axes of each the septa belonging to the first layer are disposed along a first direction, in parallel to each other, spaces between the septa of the layer being filled with air;
a rigid frame configured to support the elongate septa;
two or more slotted plates coupled to the rigid frame, each of the slotted plates defining a plurality of slots, each of the septa passing through a respective pair of slots defined by a pair of the slotted plates disposed on opposite sides of the frame from each other, such that an orientation of each of the septa with respect to the frame is determined by an orientation of the corresponding pair of slots with respect to the frame, and
a pulling mechanism disposed upon the frame, the pulling mechanism being configured to permanently apply tension to the plurality of septa that are arranged in parallel to each other, such that tension is applied to the plurality of septa by the pulling mechanism while the X-ray system directs X-rays from an X-ray source to an X-ray detector,
wherein directing the X-rays via the X-ray anti-scatter grid comprises directing the X-rays via an X-ray anti-scatter grid in which each of the septa comprises a foil core that is coated with a metal that has an atomic number that is greater than an atomic number of the foil core.

25. The method according to claim 24, wherein directing the X-rays via the X-ray anti-scatter grid comprises directing the X-rays via an X-ray anti-scatter grid that includes a single layer of elongate radiopaque septa.

26. The method according to claim 24, wherein directing the X-rays via the X-ray anti-scatter grid comprises directing the X-rays via an X-ray anti-scatter grid that further includes a second layer of elongate radiopaque septa, arranged such that longitudinal axes of each the septa belonging to the second layer are disposed along a second direction, in parallel to each other, the second direction being perpendicular to the first direction, such that, when viewed along a third direction that is perpendicular to the first and second directions, the first and second layers of radiopaque septa define a grid.

27. The method according to claim 24, wherein directing the X-rays via the X-ray anti-scatter grid comprises directing the X-rays via an X-ray anti-scatter grid in which a thickness of each of the septa is between 0.04 mm and 0.1 mm.

28. The method according to claim 24, wherein directing the X-rays via the X-ray anti-scatter grid comprises directing the X-rays via an X-ray anti-scatter grid in which a height of each of the septa is between 10 mm and 20 mm.

29. The method according to claim 24, wherein directing the X-rays via the X-ray anti-scatter grid comprises directing the X-rays via an X-ray anti-scatter grid in which, within the layer of septa, a distance between each of the septa and adjacent septa is between 0.5 mm and 1.5 mm.

30. The method according to claim 24, wherein each of the septa comprises phosphor bronze.

31. The method according to claim 24, wherein the metal coating of each of the septa comprises tin.

* * * * *